United States Patent [19]

Evans et al.

[11] Patent Number: 4,737,457

[45] Date of Patent: Apr. 12, 1988

[54] ANALYTICAL COMPOSITION, ELEMENT AND METHOD FOR THE DETERMINATION OF HYDROGEN PEROXIDE

[75] Inventors: Steven Evans; John W. Sutherland, both of Rochester, N.Y.

[73] Assignee: Eastman Kodak Company, Rochester, N.Y.

[21] Appl. No.: 832,946

[22] Filed: Feb. 26, 1986

[51] Int. Cl.$^4$ .................. C12Q 1/26; C12Q 1/28; C12Q 1/54

[52] U.S. Cl. .................. 435/14; 422/56; 435/25; 435/28; 435/805; 436/904

[58] Field of Search .................. 435/14, 25, 28, 805; 422/56; 436/904

[56] References Cited

U.S. PATENT DOCUMENTS

| | | | |
|---|---|---|---|
| 3,694,207 | 9/1972 | Matyee et al. | 96/48 |
| 3,917,452 | 11/1975 | Rittersdorf | 435/28 |
| 3,979,262 | 9/1976 | Humzicker | 195/103.5 R |
| 4,089,747 | 5/1978 | Bruschi | 195/99 |
| 4,119,405 | 10/1978 | Lam | 422/56 |
| 4,251,629 | 2/1981 | Yamanisi | 435/28 |
| 4,396,714 | 8/1983 | Maeda | 435/28 |
| 4,416,982 | 11/1983 | Tsuda | 435/28 X |
| 4,418,037 | 11/1983 | Katsuyama et al. | 422/56 |
| 4,439,527 | 3/1984 | Pakebusch | 435/28 X |
| 4,492,754 | 1/1985 | Trager | 435/28 |
| 4,503,145 | 3/1985 | Katsuyama | 435/28 X |
| 4,504,579 | 3/1985 | Sun | 435/28 |
| 4,567,139 | 1/1986 | Batz | 435/28 |

OTHER PUBLICATIONS

Gochman et al, *Clin. Chem.*, 17(12), pp. 1154–1159 (1971), Automated Determination of Uric Acid with Use of a Uricase-Peroxidase System.

Gochman et al, *Clin. Chem.*, 18(9), pp. 943–950 (1972); Application of a New Peroxide Indicator Reaction to the Specific, Automated Determination of Glucose with Glucose Oxidase.

*Primary Examiner*—Sidney Marantz
*Attorney, Agent, or Firm*—J. Lanny Tucker

[57] ABSTRACT

An analytical method for the determination of hydrogen peroxide utilizes a hydrazide or a hydrazine substituted with one or more electron withdrawing groups. The hydrazides or hydrazines react with phenolic color couplers in the presence of hydrogen peroxide and a peroxidative compound to form a dye detectable at a wavelength of 600 nm or greater. These materials can also be used to assay analytes, such as glucose and cholesterol, which can react to produce hydrogen peroxide.

20 Claims, No Drawings

ANALYTICAL COMPOSITION, ELEMENT AND METHOD FOR THE DETERMINATION OF HYDROGEN PEROXIDE

FIELD OF THE INVENTION

This invention relates to a novel composition, element and method using particular hydrazides and hydrazines to detect hydrogen peroxide or another analyte which can react to produce hydrogen peroxide. In particular, this invention relates to an assay of hydrogen peroxide or hydrogen peroxide-producing analytes in biological fluids. This invention is particularly useful in clinical chemistry.

BACKGROUND OF THE INVENTION

The detection and quantitative determination of hydrogen peroxide and compounds which yield hydrogen peroxide as a result of chemical or enzymatic reactions are of importance in many areas. For example, they are important in the determination of hydrogen peroxide produced in the enzymatic assay of various chemical or biological substances (herein identified as analytes), such as glucose, cholesterol, uric acid, triglycerides, creatine kinase, creatinine, etc., in the presence of oxygen. The quantity of analyte present in a sample is determinable from the amount of hydrogen peroxide produced.

Known compositions and methods for determining hydrogen peroxide generally comprise a substance having peroxidative activity, e.g. peroxidase, and a color dye former which undergoes a detectable change (e.g. a color change) in the presence of hydrogen peroxide and peroxidase. Various materials which are known to undergo a detectable change in such conditions include monoamines, diamines, phenols and leuco dyes. Other hydrogen peroxide indicators include hydrogen donors (identified herein as color forming compounds) which react with color couplers to produce dyes.

U.S. Pat. Nos. 4,089,747 (issued May 16, 1978 to Bruschi) and 4,119,405 (issued Oct. 10, 1978 to Lam) relate to assays for hydrogen peroxide or analytes which generate hydrogen peroxide using a combination of a hydrazone and a color coupler. Use of the hydrazones described in these references in assaying whole blood has a disadvantage. Using the hydrazones, it is difficult to obtain detectable dyes which absorb electromagnetic radiation at relatively long wavelengths, i.e. greater than about 600 nm. Dyes formed with hydrazones generally absorb at shorter wavelengths and their detection is often hindered by various spectral interferents which are present in whole blood samples. The presence of these interferents would diminish the accuracy of the assay using hydrazones in testing whole blood or serum.

SUMMARY OF THE INVENTION

The present invention overcomes the disadvantage noted above with an analytical composition which is useful for the determination of hydrogen peroxide or an analyte which will react to produce hydrogen peroxide. This composition comprises:
 a cationic mordant,
 a phenolic color coupler, and
 a color-forming compound represented by the structure

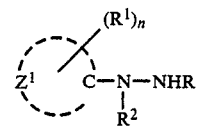

wherein R is hydrogen, $-SO_2R^3$ or $-SONR^3R^4$, $R^1$ is an electron withdrawing group, $R^2$, $R^3$ and $R^4$ are independently hydrogen, substituted or unsubstituted alkyl or substituted or unsubstituted aryl, n is an integer of 1 to 5, and $Z^1$ represents the carbon and nitrogen atoms necessary to complete a substituted or unsubstituted 5- to 10-membered aromatic carbocyclic or heterocyclic ring, provided that the color-forming compound is capable of reacting with the color coupler in the presence of the mordant to provide a dye detectable at a wavelength of 600 nm or greater.

This invention also provides a dry analytical element for the determination of hydrogen peroxide or an analyte which will react to produce hydrogen peroxide. This element comprises an absorbent carrier material and contains the analytical composition described above.

A method for the determination of hydrogen peroxide or an analyte which reacts to produce hydrogen peroxide comprises the steps of:

A. contacting a sample of a liquid suspected of containing hydrogen peroxide or an analyte which will react to produce hydrogen peroxide with the analytical composition described above, and B. detecting the dye formed as a result of the presence of hydrogen peroxide or the analyte at a wavelength equal to or greater than 600 nm.

The assay of the present invention has a number of advantages. It provides dyes in response to hydrogen peroxide which can be detected at a wavelength equal to or greater than 600 nm. Spectrophotometric detection of the dyes in this invention thereby avoids potential spectral interferents such as hemoglobin, bilirubin, etc. generally found in biological fluids.

DETAILED DESCRIPTION OF THE INVENTION

The color-forming compounds useful in the present invention are hydrazides or hydrazines substituted with one or more electron withdrawing groups which are represented by the structure:

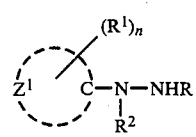

In this structure, R is hydrogen, $-SO_2R^3$ or $-SONR^3R^4$. Preferably, R is hydrogen or $-SO_2R^3$, and more preferably, it is $-SO_2R^3$. $R^2$, $R^3$ and $R^4$ are independently hydrogen, substituted or unsubstituted alkyl (preferably of 1 to 6 carbon atoms, e.g. methyl, chloromethyl, ethyl, isopropyl, etc.) or substituted or unsubstituted aryl (preferably of 6 to 10 carbon atoms, e.g. phenyl, naphthyl, p-methylphenyl, etc.). Preferably, $R^2$ is hydrogen and $R^3$ is hydrogen or substituted or unsubstituted phenyl. Also, n is an integer of 1 to 5, and preferably is 1 or 2.

R[1] is an electron withdrawing group as defined in the art. Such a group generally has a positive Hammett sigma value which is calculated according to standard procedures described, e.g. in *Steric Effects in Organic Chemistry*, John Wiley and Sons, Inc., 1956, pp. 570–574 and *Progress in Physical Organic Chemistry*, Vol. 2, Interscience Publishers, 1964, pp. 333–339. Representative electron withdrawing groups include halo (e.g. chloro, bromo, iodo, etc.), substituted or unsubstituted alkoxycarbonyl (e.g. methoxycarbonyl, ethoxycarbonyl, etc.), nitro, cyano, substituted or unsubstituted arylsulfonyl (preferably of 6 to 12 carbon atoms, e.g. phenylsulfonyl, etc.) and sulfamoyl. Nitro is a preferred electron withdrawing group.

Z represents the carbon and nitrogen atoms necessary to complete a substituted or unsubstituted 5- to 10-membered aromatic carbocyclic or heterocyclic ring. For example, the completed ring could be a phenyl, pyridinyl, pyrazinyl, quinolyl, or benzothiazolyl ring. Preferably, the ring is a substituted or unsubstituted phenyl or pyridinyl ring. Most preferably, the ring is a substituted or unsubstituted pyridinyl ring.

Representative color forming compounds useful in the practice of this invention include: 2-(benzenesulfonylhydrazino)-5-nitropyridine, 2-hydrazino-5-nitropyridine, 2-benzenesulfonylhydrazino-(N-ethyl-N-phenylsulfamoyl)-3-chloropyridine, 2-chloro-3-hydrazinopyrazine, and 2-hydrazino-3-chloro-5-sulfamoylpyridine. The first compound is a preferred one.

The color-forming hydrazines and hydrazides useful in the practice of this invention are known compounds. They can be prepared using known procedures and generally available starting materials. The hydrazines can be prepared, for example, according to the procedure described in *Org. Syn. Coll., Vol. II,* 228 (1943). The hydrazides can be prepared, for example, according to the procedure described in *Org. Syn.,* 40, 93 (1960).

The color-forming compounds described herein are used with a phenolic color coupler preferably represented by the structure:

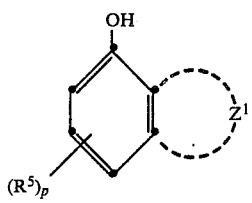

wherein $Z^1$ is as defined above, $R^5$ is hydrogen or an electron donating group as known in the art, and p is an integer of 1 to 5.

Electron donating groups generally have a negative Hammett sigma value as determined according to standard techniques described above. Representative electron donating groups include substituted or unsubstituted alkyl (preferably of 1 to 6 carbon atoms, e.g. methyl, ethyl, aminometyl, isopropyl, etc.), substituted or unsubstituted alkoxy (preferably of 1 to 6 carbon atoms, e.g. methoxy, ethoxy, isopropoxy, etc.), substituted or unsubstituted dialkylamino (preferably having from 1 to 6 carbon atoms in the alkyl portion), hydroxy, sulfonamido and acetamido. Preferred electron donating groups are hydroxy, alkoxy or dialkylamino as defined above.

These color couplers are known compounds and can be prepared using known procedures and starting materials.

Representative color couplers include 1,7-naphthalenediol, 2,6-dimethoxyphenol, m-dimethylaminophenol, 2,7-naphthalenediol, 1-naphthol-8-sulfonic acid, 8-amino-1-amino-1-naphthol, 1-naphthol and 2,3-dimethylphenol. Preferred couplers include 1,7-napthalenediol, 2,6-dimethoxyphenol and 1-naphthol.

In the practice of this invention, the color-forming compounds and color couplers described herein are used in combination with a cationic mordant. Such a mordant is a polymeric material having one or more positive charges placed along the polymeric backbone directly thereon or on side chains. Cationic mordants are known in the art and described, for example, in U.S. Pat. Nos. 3,958,995 (issued May 25, 1976 to Campbell et al), 4,069,017 (issued Jan. 17, 1978 to Wu et al), 4,124,386 (issued Nov. 7, 1978 to Yoshida et al) and 4,247,615 (issued Jan. 27, 1981 to McGuckin et al) and *Research Disclosure,* publication 12045 (April, 1974) which is available from Kenneth Mason Publications, Ltd., The Old Harbourmaster's, 8 North Street, Emsworth, Hamsphire, P010 7DD, England. Procedures for making such mordants are described in these and other published references.

Representative useful mordants include:
poly(styrene-co-N-benzyl-N,N-dimethyl-N-vinylbenzylammonium chloride-co-divinylbenzene),
poly(N,N,N-trimethyl-N-vinylbenzylammonium chloride),
poly(N,N,N-trioctyl-N-vinylbenzylphosphonium chloride),
poly(styrene-co-N-vinylbenzyl-N,N,N-trihexylammonium chloride), and the like.

The analytical composition of this invention can be used in both solution and dry assays, and comprises the color-forming compound, phenolic color coupler and cationic mordant described above. The composition is preferably used with, or includes, a substance having peroxidative activity.

Substances having peroxidative activity are also known as peroxidative substances and are capable of catalyzing the oxidation of another substance by means of hydrogen peroxide and other peroxides. Such substances include natural and synthetic peroxidases, cytochromes, hemin, forms of hemoglobin, alkaline hematin, iron sulfocyanate, iron tannate, chromic salts and the like. Peroxidase is a particularly useful peroxidative substance.

Substantially any buffer can be used with the composition of this invention. Buffers are generally used to provide a pH in the assay which is conducive to dye formation. Generally, the pH is kept within the range of from about 4 to about 9, but a specific pH will depend to some extent on the particular analyte being assayed. Useful buffers include carbonates, borates, phosphates, glutarates, the tris materials, e.g. tris(hydroxmethyl)aminomethane and others known in the art.

The compositions of this invention can be prepared for use in a solution assay by mixing the components of the analytical composition in water or a buffer. If the color-forming compounds, phenolic couplers and mordants have limited solubility in water, they can be dissolved in a water-miscible solvent, such as an alcohol or N,N-dimethylformamide, prior to mixing. The peroxidative substance can be mixed in as well. The details of preparing representative analytical compositions are given in Examples 1-5 below.

When the compositions of this invention are used in solution assays, generally the color-forming compound is present in a concentration of at least about 1, and preferably from about 5 to about 50, μg/ml of solution. The color coupler is generally present in a concentration of at least about 1, and preferably from about 5 to about 50, μg/ml of solution. The cationic mordant is generally present in an amount of at least about 0.1, and preferably from about 0.5 to about 1, μg/ml of solution. The peroxidative substance can be present in an amount sufficient to catalyze the dye-forming reaction. For example, peroxidase can be generally present in an amount of at least about 0.01, and preferably from about 1 to about 10, I.U./ml. The amounts of other addenda generally used (e.g. buffer, surfactant, etc.) and of the interactive composition (described below) are within the skill of a worker in the art.

The compositions of this invention can be used to determine hydrogen peroxide or an analyte which is capable of producing hydrogen peroxide, i.e. an analyte which can participate in one or more reactions which produce hydrogen peroxide. To determine such analytes, the analytical composition described above is combined with an interactive composition with which the analyte will react to produce hydrogen peroxide in one or more reactions. Analytes which can be determined in this manner include glucose, triglycerides, uric acid, cholesterol, galactose, amino acids, creatine kinase, creatinine, and others known to one skilled in the clinical chemistry art. Specific interactive compositions for a given analyte can be readily determined by one of ordinary skill in the art.

The present invention is adaptable to both solution and dry assays. In a solution assay, generally the analytical composition, peroxidative substance and interactive composition, if included, are contacted with a liquid test sample suspected of containing hydrogen peroxide or another analyte by mixing in a suitable container (e.g. test tube, petri dish, beaker, cuvette, etc.). The resulting solution is incubated for a relatively short time (i.e. about 5 minutes) at a temperature of up to about 45° C. The sample is then evaluated by measuring the amount of dye provided as a result of the presence of hydrogen peroxide. The amount of dye can then be correlated to the amount of hydrogen peroxide either initially present in the sample, or produced as a result of the presence of an analyte. Such an evaluation can be done visually or with suitable colorimetric detection equipment and procedures at a wavelength greater than or equal to 600 nm.

Alternatively, the method of this invention can be practiced with a dry analytical element which is comprised of an absorbent carrier material, i.e. self-supporting absorbent sheet or pressed material, such as filter paper or strips, which contains the analytical composition and optionally, any other desired reagents, e.g. the peroxidative substance. Such elements are known in the art as test strips, diagnostic elements, dip sticks, diagnostic agents and the like.

When employed in dry elements, the composition of this invention can be incorporated into a suitable carrier material by imbibition, impregnation, coating or another suitable technique. Useful carrier materials are insoluble and maintain their structural integrity when exposed to water or physiological fluids such as urine or serum. Useful elements can be prepared from paper, porous particulate structures, cellulose, wood, glass fibers, woven and nonwoven fabrics (synthetic and nonsynthetic) and the like. A useful dry analytical element is made by imbibing a solution of the analytical composition into the material and drying. Useful materials and procedures for making such elements are well known in the art as exemplified in U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and U.K. Pat. No. 2,052,057 (published Jan. 21, 1981).

Preferably, the dry analytical elements of this invention have at least one porous spreading zone. This zone can be a self-supporting carrier material as described above, but preferably it is carried on a separate nonporous support. Such a support can be any suitable dimensionally stable, and preferably, transparent (i.e. radiation transmissive) material which transmits electromagnetic radiation of a wavelength between about 200 and about 900 nm. A support of choice for a particular element should be compatible with the intended mode of detection (reflection, transmission or fluoroescence spectroscopy). Useful support materials include paper, metal foils, polystyrene, polyesters [e.g. poly(ethylene terephthalate)], polycarbonates, cellulose esters (e.g. cellulose acetate), etc.

The porous spreading zone can be prepared from any suitable fibrous or non-fibrous material or mixtures of either or both. The void volume and average pore size of this zone can be varied depending upon the type of liquid sample to be applied.

Useful spreading zones can be prepared as described, for example, in U.S. Pat. Nos. 4,292,272 (issued Sept. 29, 1981 to Kitajima et al), 3,992,158 (issued Nov. 16, 1976 to Przybylowicz et al), 4,258,001 (issued Mar. 24, 1981 to Pierce et al), and 4,430,436 (issued Feb. 7, 1984 to Koyama et al) and Japanese Patent Publication No. 57(1982)-101760 (published June 24, 1982). It is desirable that the spreading zone be isotropically porous, meaning that the porosity is the same in each direction in the zone as created by interconnected spaces or pores between particles, fibers, polymeric strands, etc.

The elements can have more than one zone, e.g. one or more reagent zones, spreading zones, registration zones, mordant zones, radiation-blocking or filter zones, subbing zones, barrier zones, buffer zones, etc. The zones are generally in fluid contact with each other meaning that fluids, reagents and reaction products can pass between superposed regions of adjacent zones. Preferably, the zones are separately coated superposed layers, although multiple zones can be in a single layer.

The components of the analytical composition of this invention, as well as the peroxidative substance, interactive composition, buffer, etc. can be incorporated in any of the element zones. The location of individual components is within the skill of a worker in the clinical chemistry art.

In the elements of this invention, the amount of the composition components can be varied widely. Generally the color-forming compound is present in a coverage of at least about 10, and preferably from about 30 to about 300, mg/m$^2$. The phenolic color coupler is generally present in a coverage of at least about 10, and preferably from about 30 to about 300, mg/m$^2$. The cationic mordant is generally present in a coverage of at least about 1, and preferably from about 5 to about 25, mg/m². The peroxidative substance can be present in a coverage generally of at least about 25,000, and preferably from about 50,000 to about 100,000 I.U./m² for peroxidase. A variety of other desirable, but optional reagents and addends can be present in the element in amounts known to one skilled in the art. Such materials include surfactants, buffers, binders, pigments, activators, reagents of an interactive composition, etc.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, hydrogen peroxide or analyte determination is made by taking the element from a supply roll, chip packet or other source and physically contacting it with a sample (e.g. 1-200 μl) of the liquid to be tested such that the sample mixes with the reagents within the element. Such contact can be accomplished in any suitable manner, e.g. dipping orr immersing the element into the sample or, preferably, by spotting the element by hand or machine with a drop of the sample using a suitable dispensing means.

After sample application, the element is exposed to any conditioning, such as incubation, heating or the like, that may be desirable to quicken or otherwise facilitate obtaining any test result.

Determination of hydrogen peroxide or an analyte is achieved when the color-forming compound and phenolic coupler react to form a dye. This dye can be detected with the unaided eye or with suitable spectrophotometric means and procedures at a wavelength greater than or equal to 600 nm. Generally, the dyes formed in the practice of this invention have a $\lambda_{max}$, or an absorption maximum, equal to or greater than 600 nm.

The following preparations and examples are provided to illustrate the practice of the invention. In those examples, the materials were obtained as follows:

ZONYL FSN surfactant from DuPont (Wilmington, Del., U.S.A.), glucose oxidase, and peroxidase from Sigma Chemical Co. (St. Louis, Mo., U.S.A.), and the remainder from Eastman Kodak Company (Rochester, N.Y., U.S.A.) or prepared using commercially available starting materials and known procedures.

As used in the context of this disclosure, I.U. represents the International Unit for enzyme activity defined as one I.U. being the amount of enzyme activity required to catalyze the conversion of 1 micromole of substrate per minute under standard pH and temperature conditions for the enzyme.

EXAMPLES 1–8

Solution Assay of Hydrogen Peroxide with Various Couplers

These examples illustrate the practice of this invention to determine hydrogen peroxide in solution assays using a particular color-forming compound and various phenolic couplers.

Analytical compositions of this invention were prepared, each comprised of: the color-forming compound 2-(benzenesulfonylhydrazino)-5-nitropyridine (0.1 ml of 0.025% solution in methanol), a color coupler as noted in Table I below (0.1 ml of 0.025% solution in methanol), 0.2 ml of a 1.8% latex dispersion of the mordant poly(styrene-co-N-benzyl-N,N-dimethyl-N-vinylbenzyl ammonium chloride-co-divinylbenzene) (99:99:2 molar ratio), and phosphate buffer (pH 8) to 4 ml.

Control compositions were similarly constituted but absent the mordant latex.

Peroxidase (0.1 ml of 0.2% in pH 7 phosphate buffer) and a test sample (1 drop) containing 3% hydrogen peroxide were added to each solution. Each resulting assay solution was shaken and the hue and intensity (optical density, O.D.) of the resulting dye were observed after color formation was complete (0.5 to 5 minutes). The Control assays provided dyes having little or no absorption above 600 nm as noted in Table I below. The compositions of this invention, however, provided dyes which had significant absorption at or above 600 nm as noted in Table I below. Dye densities were measured against a blank containing all of the components and invention compositions except hydrogen peroxide.

TABLE I

Reaction of Various Couplers with 2-Benzene Sulfonylhydrazino-5-Nitropyridine and $H_2O_2$ in the Presence of Peroxidase

| Example | Color Coupler | | 550 nm | 600 nm | 625 nm | 650 nm | 750 nm |
|---|---|---|---|---|---|---|---|
| 1 | 1,7-naphthalenediol | C* | 0.11 | 0.08 | 0.07 | 0.06 | 0.03 |
|   |   | I | 0.05 | 0.35 | 0.55 | 0.70 | 0.07 |
| 2 | 2,6-dimethoxyphenol | C | 0.10 | 0.03 | 0.03 | 0.03 | 0.01 |
|   |   | I | 0.28 | 0.86 | 1.17 | 1.05 | 0.04 |
| 3 | 1-naphthol | C | 0.14 | 0.12 | 0.12 | 0.11 | 0.05 |
|   |   | I | 0.18 | 0.86 | 1.17 | 1.00 | 0.02 |
| 4 | 2,3-dimethylphenol | C | 0.04 | 0.04 | 0.04 | 0.03 | 0.02 |
|   |   | I | 0.12 | 0.15 | 0.15 | 0.10 | 0.06 |
| 5 | m-dimethylamino phenol | C | 0.07 | 0.06 | 0.05 | 0.04 | 0.03 |
|   |   | I | 0.17 | 0.32 | 0.23 | 0.14 | 0.01 |
| 6 | 8-amino-2-naphthol | C | 0.07 | 0.06 | 0.05 | 0.04 | 0.03 |
|   |   | I | 0.15 | 0.17 | 0.24 | 0.23 | 0.06 |
| 7 | 1-naphthol-8-sulfonic acid | C | 0.06 | 0.07 | 0.07 | 0.06 | 0.02 |
|   |   | I | 0.14 | 0.15 | 0.16 | 0.14 | 0.07 |
| 8 | 3,6-dichlorophenol | C | 0.03 | 0.02 | 0.02 | 0.02 | 0.01 |
|   |   | I | No Color Change When $H_2O_2$ Added | | | | |

*C = Control Solution
I = Invention Test Solution

EXAMPLES 9-12

Solution Assay for Hydrogen Peroxide Using Various Color-Forming Compounds

These examples are like Examples 1-8 except the same color coupler (1-naphthol) was used at two concentrations with several color-forming compounds as shown in Table II below. The assays were performed as described in Examples 1-8.

The assays provided dyes which have significant absorption at or greater than 600 nm as noted in Table II below. It was observed that the Control solutions (i.e. no mordant) had some turbidity which contributed to most of the optical density. Little or no turbidity was observed in the solutions containing mordant. In Examples 12, 13, 15 and 17, color formation was low at low concentrations of 1-naphthol.

TABLE II

Reaction of Various Color Formers With $H_2O_2$ and 1-Naphthol in the Presence of Peroxidase at pH 8

| Example | Color Former | 1-Naphthol Concentration (mg/ml) | ** | Optical Density @ 550 nm | 600 nm | 625 nm | 650 nm | 750 nm |
|---|---|---|---|---|---|---|---|---|
| 9 | $NO_2$-pyridine-NH-N(H)-$SO_2$-phenyl | I* 6.25 | + | .30 | 1.41 | 1.88 | 1.55 | .01 |
|   |   | C 6.25 | − | .18 | .15 | .14 | .09 | .06 |
| 10 | Et,Pn-$NO_2S$-pyridine(Cl)-NH-N(H)-$SO_2$-phenyl | I 6.25 | + | .41 | .48 | .08 | .00 | .00 |
|   |   | C 6.25 | − | .17 | .14 | .12 | .10 | .06 |
| 11 | pyridine-NH-N(H)-$SO_2$-phenyl-$CH_3$ | I { 62.5 | + | .59 | .52 | .48 | .45 | .34 |
|   |   | 5.25 | + | No Color Change When $H_2O_2$ Added | | | | |
|   |   | C 6.25 | − | .18 | .15 | .14 | .13 | .08 |
| 12 | pyrazole-N(H)-$NH_2$ | I { 62.5 | + | .36 | .29 | .26 | .21 | .16 |
|   |   | 6.25 | + | .02 | .02 | .01 | .00 | .00 |
|   |   | C 6.25 | − | .18 | .14 | .13 | .12 | .07 |
| 13 | pyrazole(Cl)-N(H)-$NH_2$ | I { 62.5 | + | .69 | .60 | .42 | .30 | .20 |
|   |   | 6.25 | + | .08 | .07 | .02 | .00 | .00 |
|   |   | C 6.25 | − | .21 | .18 | .16 | .13 | .07 |
| 14 | $O_2N$-pyridine-N(H)-$NH_2$ | I 6.25 | + | .09 | .25 | .32 | .28 | .02 |
|   |   | C 6.25 | − | .18 | .15 | .14 | .13 | .07 |
| 15 | $NH_2O_2S$-pyridine(Cl)-N(H)-$NH_2$ | I { 62.5 | + | .84 | .73 | .56 | .42 | .29 |
|   |   | 6.25 | + | .12 | .11 | .05 | .02 | .01 |
|   |   | C 6.25 | − | .22 | .20 | .18 | .13 | .05 |
| 16 | $NO_2$-phenyl-NH-$NH_2$ | I 62.5 | + | .37 | .32 | .28 | .26 | .19 |
|   |   | C 6.25 | − | .11 | .09 | .08 | .07 | .04 |

TABLE II-continued

Reaction of Various Color Formers With H₂O₂ and 1-Naphthol
in the Presence of Peroxidase at pH 8

| Example | Color Former | 1-Naphthol Concentration (mg/ml) | ** | Optical Density @ 550 nm | 600 nm | 625 nm | 650 nm | 750 nm |
|---|---|---|---|---|---|---|---|---|
| 17 |  | I { 62.5 | + | .23 | .16 | .14 | .12 | .09 |
| | | 6.25 | + | .04 | .01 | .00 | .00 | .00 |
| | | C  6.25 | − | .14 | .11 | .09 | .08 | .04 |

*I = Invention
C = Control
** + Refers to the presence of mordant
− Refers to the absence of mordant

EXAMPLE 13

Dry Assay of Glucose Using Dry Analytical Element

This example illustrates the assay of glucose in a test liquid using a dry analytical element having the format and components illustrated below.

| | | |
|---|---|---|
| Spreading Layer | Poly(vinyl toluene-co-p-t-butylstyrene-co-methacrylic acid) (61:37:2 weight ratio) beads | 50–150 g/m² |
| | Poly(vinyl pyrrolidone) | 0.5–15 g/m² |
| | Glucose oxidase | 20,000–50,000 I.U./m² |
| | Peroxidase | 20,000–50,000 I.U./m² |
| | Potassium phosphate buffer (pH 6.5) | 1–10 g/m² |
| | ZONYL FSN surfactant | 0.1–1 g/m² |
| Registration Layer | 1,7-Dihydroxy naphthalene | 0.05–0.5 g/m² |
| | 2-(Benzenesulfonylhydrazino)-5-nitropyridine | 0.1–1 g/m² |
| | Poly(styrene-co-N—benzyl-N,N—dimethyl-N—vinyl benzyl ammonium chloride-co-divinylbenzene) (99:99:2 molar weight) | 0.5–5 g/m² |
| | Poly(vinyl pyrrolidone) | 0.1–2 g/m² |
| Subbing Layer | Gelatin (hardened) | 5–20 g/m² |
| | Poly(ethylene terephthalate) Support | |

Samples (10 μl) of test liquids containing various amounts of either hydrogen peroxide or glucose were applied to the spreading layer of the element. The reflection density ($D_R$) of the resulting dye in the element was measured at 650 nm after incubation at 37° C. for 5 minutes using a commercially available spectrophotometer. The resulting densities are recorded in Table III below. Dye density was proportional to the amount of analyte in the test liquid. A Control liquid containing no analyte was similarly tested.

TABLE III

| Hydrogen Peroxide | | Glucose | |
|---|---|---|---|
| Concentration (mmolar) | $D_R$ | Concentration (mg/dl) | $D_R$ |
| 0 | 0.56 | 0 | 0.72 |
| 2.5 | 1.15 | 12.5 | 1.17 |
| 5 | 1.61 | 25 | 1.41 |
| 10 | 2.02 | 50 | 1.7 |
| 20 | 2.22 | 100 | 2.05 |

The invention has been described in detail with particular reference to preferred embodiments thereof, but it will be understood that variations and modifications can be effected within the spirit and scope of the invention.

We claim:

1. An analytical composition for the determination of hydrogen peroxide or an analyte which reacts to produce hydrogen peroxide comprising:
   a cationic mordant,
   a phenolic color coupler, and
   a color-forming compound represented by the structure

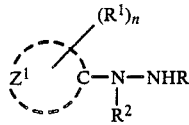

wherein R is hydrogen, —SO₂R³ or —SONR³R⁴, R¹ is an electron withdrawing group, R², R³ and R⁴ are independently hydrogen, substituted or unsubstituted alkyl or substituted or unsubstituted aryl, n is an integer of 1 to 5, and Z¹ represents the carbon and nitrogen atoms necessary to complete a substituted or unsubstituted 5- to 10-membered aromatic carbocyclic or heterocyclic ring,
provided said color-forming compound is capable of reacting with said color coupler in the presence of said mordant to provide a dye detectable at a wavelength of 600 nm or greater.

2. The analytical composition of claim 1 wherein R is hydrogen or —SO₂R³, R² is hydrogen, R³ is hydrogen or substituted or unsubstituted phenyl, n is 1 or 2, and Z¹ represents the carbon and nitrogen atoms necessary to complete a substituted or unsubstituted 6-membered phenyl or pyridyl.

3. The analytical composition of claim 2 wherein R¹ is nitro and Z represents the carbon and nitrogen atoms necessary to complete a substituted or unsubstituted pyridyl ring.

4. The analytical composition of claim 1 wherein said color-forming compound is 2-(benzenesulfonylhydrazino)-5-nitropyridine.

5. The analytical composition of claim 1 further comprising a substance having peroxidative activity.

6. The analytical composition of claim 1 wherein said peroxidative compound is peroxidase.

7. The analytical composition of claim 1 wherein said mordant is poly(styrene-co-N-benzyl-N,N,dimethyl-N-vinylbenzylammonium chloride-co-divinylbenzene).

8. The analytical composition of claim 1 further comprising a buffer to maintain the pH at from about 4 to about 9.

9. The analytical composition of claim 1 wherein said phenolic color coupler is represented by the structure

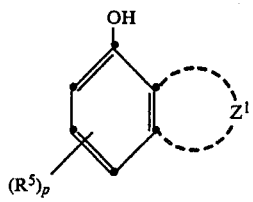

wherein $Z^1$ is as defined above, $R^5$ is hydrogen or an electron donating group, and p is an integer of 1 to 5.

10. An analytical composition for the determination of an analyte comprising:
an interactive composition which produces hydrogen peroxide upon interaction with an analyte,
a cationic mordant,
a phenolic color coupler, and
a color-forming compound represented by the structure

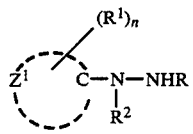

wherein R is hydrogen, $-SO_2R^3$ or $-SONR^3R^4$, $R^1$ is an electron withdrawing group, $R^2$, $R^3$ and $R^4$ are independently hydrogen, substituted or unsubstituted alkyl or substituted or unsubstituted aryl, n is an integer of 1 to 5, and $Z^1$ represents the carbon and nitrogen atoms necessary to complete a substituted or unsubstituted 5- to 10-membered aromatic carbocyclic or heterocyclic ring,
provided said color-forming compound is capable of reacting with said color coupler in the presence of said mordant to provide a dye detectable at a wavelength of 600 nm or greater.

11. The analytical composition of claim 10 further comprising a buffer which maintains the pH at from about 4 to about 9 and a substance having peroxidative activity.

12. The analytical composition of claim 10 wherein said peroxidative composition is peroxidase and said interactive composition comprises glucose oxidase.

13. A dry analytical element for the determination of hydrogen peroxide or an analyte which will react to produce hydrogen peroxide comprising an absorbent material and containing
a cationic mordant,
a phenolic color coupler, and
a color-forming compound represented by the structure

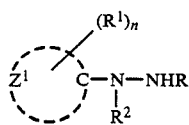

wherein R is hydrogen, $-SO_2R^3$ or $-SONR^3R^4$, $R^1$ is an electron withdrawing group, $R^2$, $R^3$ and $R^4$ are independently hydrogen, substituted or unsubstituted alkyl or substituted or unsubstituted aryl, n is an integer of 1 to 5, and $Z^1$ represents the carbon and nitrogen atoms necessary to complete a substituted or unsubstituted 5- to 10-membered aromatic carbocyclic or heterocyclic ring,
provided said color-forming compound is capable of reacting with said color coupler in the presence of said mordant to provide a dye detectable at a wavelength of 600 nm or greater.

14. The element of claim 13 further comprising a substance having peroxidative activity.

15. The element of claim 13 further comprising an interactive composition which produces hydrogen peroxide upon interaction with an analyte.

16. A dry analytical element for the determination of an analyte which will react to produce hydrogen peroxide comprising a support having thereon, in order and in fluid contact, a registration layer and a porous spreading layer,
said element also containing
an interactive composition which produces hydrogen peroxide upon interaction with said analyte,
peroxidase,
a phenolic color coupler,
a cationic polymeric mordant, and
a color-forming compound represented by the structure

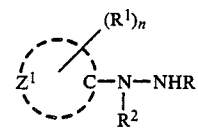

wherein R is hydrogen, $-SO_2R^3$ or $-SONR^3R^4$, $R^1$ is an electron withdrawing group, $R^2$, $R^3$ and $R^4$ are independently hydrogen, substituted or unsubstituted alkyl or substituted or unsubstituted aryl, n is an integer of 1 to 5, and $Z^1$ represents the carbon and nitrogen atoms necessary to complete a substituted or unsubstituted 5- to 10-membered aromatic carbocyclic or heterocyclic ring,
provided that said color-forming compound is capable of reacting with said color coupler in the presence of said mordant to provide a dye detectable at a wavelength of 600 nm or greater.

17. The element of claim 16 wherein said interactive composition comprises glucose oxidase.

18. A method for the determination of hydrogen peroxide or an analyte which will react to produce hydrogen peroxide comprising the steps of:
A. contacting a sample of a liquid suspected of containing hydrogen peroxide or an analyte which will react to produce hydrogen peroxide with
a substance having peroxidative activity,
a cationic mordant,
a phenolic color coupler, and
a color-forming compound represented by the structure

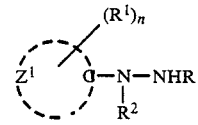

wherein R is hydrogen, $-SO_2R^3$ or $-SONR^3R^4$, $R^1$ is an electron withdrawing group, $R^2$, $R^3$ and $R^4$ are independently hydrogen, substituted or unsubstituted alkyl or substituted or unsubstituted aryl, n is an integer of 1 to 5, and $Z^1$ represents the carbon and nitrogen atoms necessary to complete a substituted or unsubstituted 5- to 10-membered aromatic carbocyclic or heterocyclic ring, and B. detecting the dye formed as a result of the presence of hydrogen peroxide or said analyte at a wavelength equal to or greater than 600 nm.

19. The method of claim 18 for the determination of an analyte which reacts to produce hydrogen peroxide carried out in the presence of an interactive composition for said analyte.

20. The method of claim 19 for the determination of glucose with an interactive composition comprising glucose oxidase.

* * * * *